United States Patent
Boyd, III et al.

[11] Patent Number: 5,360,409
[45] Date of Patent: Nov. 1, 1994

[54] SYRINGE HOLDER WITH RETRACTABLE NEEDLE ASSEMBLY

[76] Inventors: Henry Boyd, III, 3217-H Orange St., Greensboro, N.C. 27406; Lester Best, Jr., 300-F Edward St., Greensboro, N.C. 27419

[21] Appl. No.: 32,678

[22] Filed: Mar. 17, 1993

[51] Int. Cl.⁵ ............................................. A61M 5/32
[52] U.S. Cl. .................................... 604/198; 604/232; 604/263
[58] Field of Search ............... 604/198, 195, 232, 263, 604/192, 218, 187

[56] References Cited

U.S. PATENT DOCUMENTS

| | | | |
|---|---|---|---|
| D. 313,470 | 1/1991 | Talonn et al. | D24/24 |
| 2,876,770 | 6/1959 | White. | |
| 2,994,323 | 4/1961 | Dann et al. | |
| 3,253,592 | 5/1966 | Von Pechmann. | |
| 3,410,267 | 11/1968 | Nojd. | |
| 3,848,593 | 1/1974 | Baldwin. | |
| 4,767,413 | 4/1988 | Haber et al. | |
| 4,813,426 | 7/1989 | Haber et al. | |
| 4,820,275 | 8/1989 | Haber et al. | |
| 4,911,693 | 3/1990 | Paris | 604/192 |
| 4,917,672 | 4/1990 | Terndrup et al. | 604/192 |
| 4,927,416 | 5/1990 | Tomkiel | 604/263 X |
| 4,929,237 | 5/1990 | Medway | 604/198 |
| 5,088,986 | 2/1992 | Nusbaum | 604/195 |
| 5,092,851 | 3/1992 | Ragner | 604/192 |
| 5,106,379 | 4/1992 | Leap | 604/198 |
| 5,135,510 | 8/1992 | Maszkiewicz et al. | 604/195 |

FOREIGN PATENT DOCUMENTS 2264835 11/1935 Australia.
WO8910767 11/1989 WIPO.

*Primary Examiner*—John D. Yasko
*Attorney, Agent, or Firm*—Rhodes Coates & Bennett

[57] ABSTRACT

A syringe holder for a conventional disposable syringe. The holder includes a needle assembly having a retractable needle for preventing accidental needle pricks. The needle assembly mounts to the forward end of a carrier having a chamber for receiving a hypodermic syringe. A plunger is slidably mounted in the carrier for moving the syringe between a loading/unloading position and a "use" position. As the hypodermic syringe is moved from its loading/unloading position to its "use" position, the hypodermic needle is extended through an aperture in the needle cap to expose the hypodermic needle. A locking means locks the hypodermic syringe in the "use" position during administration of medication to or drawing fluid from a patient. After use, the locking means is released and the needle is urged to a retracted position by a biasing means. The needle assembly and hypodermic syringe then are discarded.

15 Claims, 4 Drawing Sheets

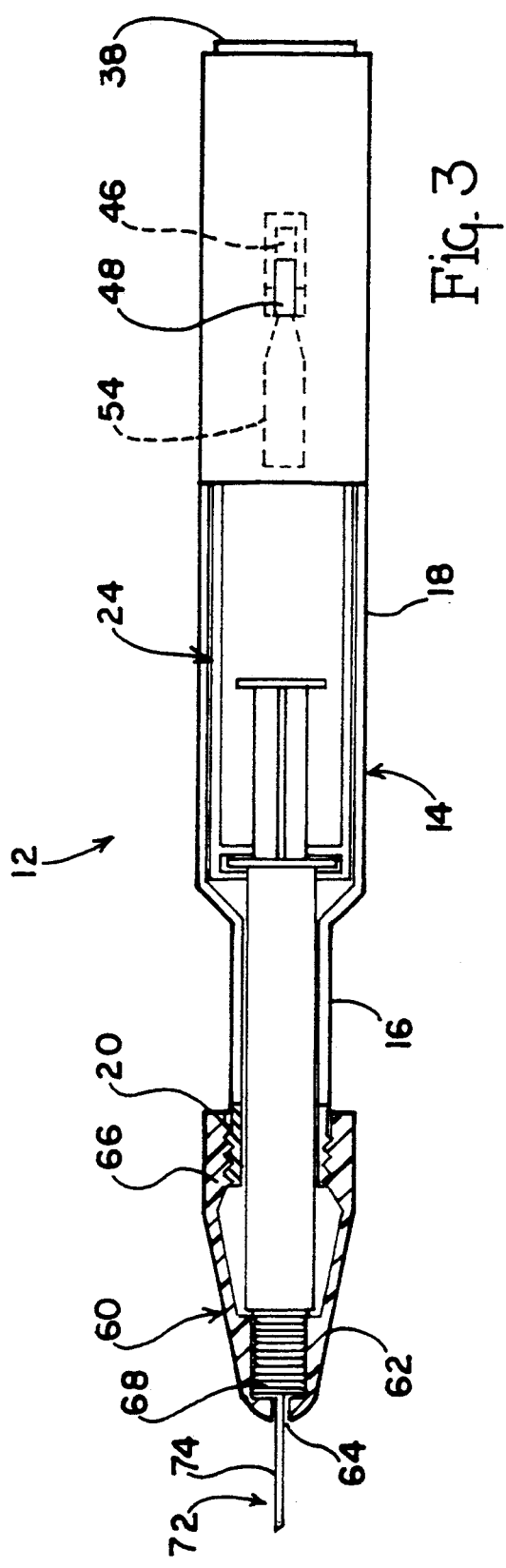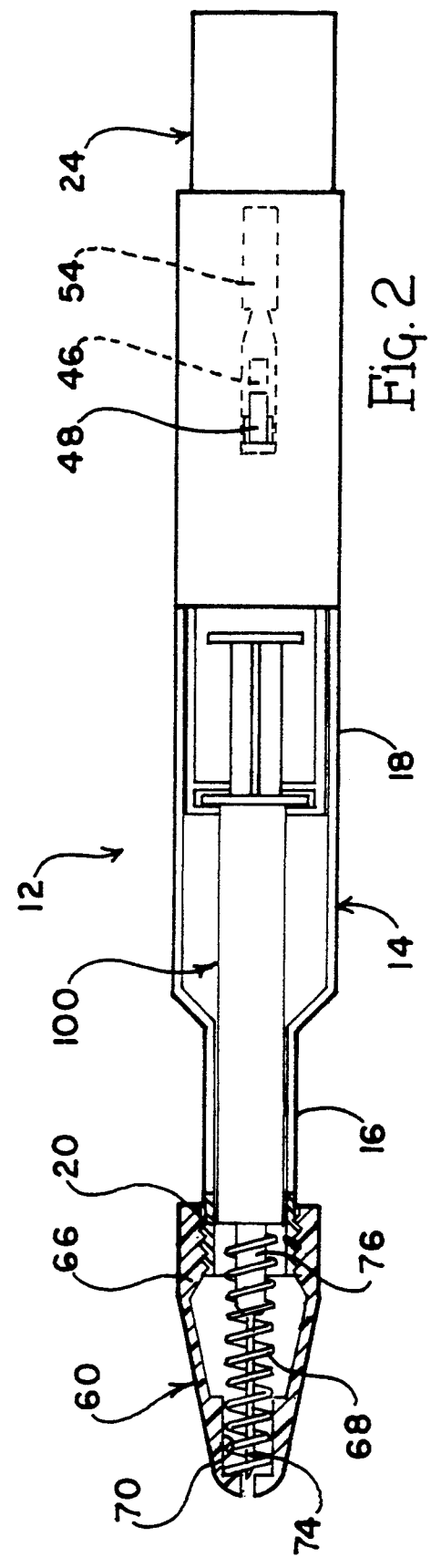

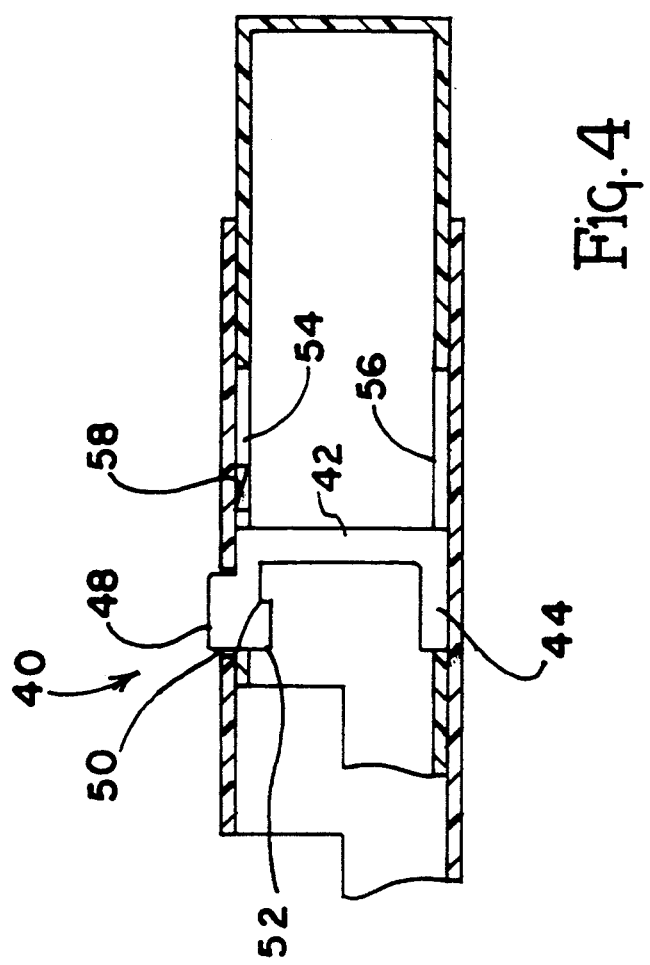

SYRINGE HOLDER WITH RETRACTABLE NEEDLE ASSEMBLY

BACKGROUND OF THE INVENTION (1) Field of the Invention

The present invention relates generally to hypodermic syringes and, more particularly, to a syringe holder for a hypodermic syringe to prevent accidental needle pricks.

(2) Description of the Prior Art

Syringes are often used for administering medication to or drawing body fluids from patients suffering from infectious diseases. Numerous cases have been reported in which doctors, nurses, or other medical personnel have been infected by accidental needle pricks. The seriousness of the problem has become more acute in light of the recent spread of Acquired Immune Deficiency Syndrome (AIDS). Accordingly, it is of utmost importance that extreme care be exercised in the handling and disposal of hypodermic syringes after use to prevent the accidental transmission of the HIV virus, as well as other infectious diseases.

In the past, various types of guards or shielding devices have been devised for hypodermic needles to prevent accidental needle pricks. Typically, a guard is slidably mounted on the syringe barrel and is moveable from an extended position in which the protective shield overlies the needle to a retracted position in which the needle is exposed. A latching mechanism of some type is commonly provided for locking the shield in the extended position.

While the prior art protective shields are capable of preventing accidental needle pricks, such prior art devices have not been widely use. One drawback is that most prior art devices can be used only with specially designed syringes which are generally more costly to produce than conventional disposable syringes.

Thus, there remains a need for a new and improved syringe holder and needle guard which is operable to prevent accidental needle pricks while, at the same time, is adapted to use a conventional disposable syringe.

SUMMARY OF THE INVENTION

The present invention is directed to a reusable cartridge holder having a retractable needle assembly for use with a conventional disposable syringe. The cartridge holder comprises a generally cylindrical sleeve having a cavity for receiving the hypodermic syringe. The syringe is loaded into the cavity of the cartridge holder through an opening in the side of the housing. A needle assembly is attached to a forward end of the cartridge holder. The needle assembly includes a hypodermic needle which engages with the hypodermic syringe loaded in the cartridge holder. A plunger is mounted in the cartridge holder for moving the syringe from its initial "loading" position to a "use" position. The carrier pushes the hypodermic syringe forwardly in the cartridge holder which causes the hypodermic needle to extend from the needle assembly. A locking mechanism locks the plunger in place while medication is administered to or fluid drawn from the patient. After administering the medication or drawing the fluid, the locking mechanism is released. A biasing member in the needle assembly causes the hypodermic syringe and plunger to be pushed back to the initial "loading" position. The hypodermic syringe and needle assembly are then removed and discarded. The cartridge holder can be sterilized and reused.

Accordingly, one aspect of the present invention is to provide a syringe holder. The syringe holder includes: (a) a carrier having a chamber for receiving a hypodermic syringe, the syringe being moveable within the carrier between a loading/unloading position and a use position; (b) a needle assembly detachably secured at a forward end of the carrier including a retractable needle normally disposed in a retracted position, the needle being moveable to an extended position when the syringe is moved from its loading/unloading position to its use position; and (c) locking means for locking the hypodermic syringe in its use position during administration of medication to or drawing fluid from a patient.

Another aspect of the present invention is to provide a syringe holder. The syringe holder includes: (a) a carrier having a forward end, a rear end, and a chamber for receiving a hypodermic syringe, the syringe being moveable within the chamber between a loading/unloading position and a use position; (b) a needle assembly detachably secured at the forward end of the carrier, the needle assembly including: (1) a needle cap having one closed end and one open end; (2) an aperture formed in the closed end of the needle cap; (3) a needle mounted within the needle cap so as to moveable between a retracted position within the needle cap and an extended position in which the needle projects through the aperture of the needle cap; (4) a coil spring for biasing the needle to its retracted position, the coil spring forming a longitudinally compressible sheath around the needle when the needle is in the retracted position; and (c) locking means for locking the hypodermic syringe in its use position during administration of medication to or drawing fluid from a patient.

Still another aspect of the present invention is to provide a needle assembly for a syringe holder. The needle assembly includes: (a) a needle assembly having one closed end and one open end; (b) an aperture formed in the closed end of the needle cap; (c) a needle mounted within the needle cap so as to move between a retracted position within the needle cap and an extended position in which the need projects through the aperture of the needle cap; and (d) a coil spring for biasing the needle to its retracted position, the coil spring forming a longitudinally compressible sheath around the needle when the needle is in the retracted position.

These and other aspects of the present invention will become apparent to those skilled in the art after a reading of the following description of the preferred embodiment when considered with the drawings.

BRIEF DESCRIPTION OF THE DRAWINGS

FIG. 2 is a top plan view of the cartridge holder of the present invention with a portion shown in section and the hypodermic syringe shown in a "loading" position;

FIG. 3 is a top plan of the cartridge holder with a portion shown in section and the hypodermic syringe shown in a "use" position;

FIG. 4 is a partial section view of the cartridge holder taken along the centerline thereof to illustrate the locking mechanism.

DESCRIPTION OF THE PREFERRED EMBODIMENTS

Figure 1:
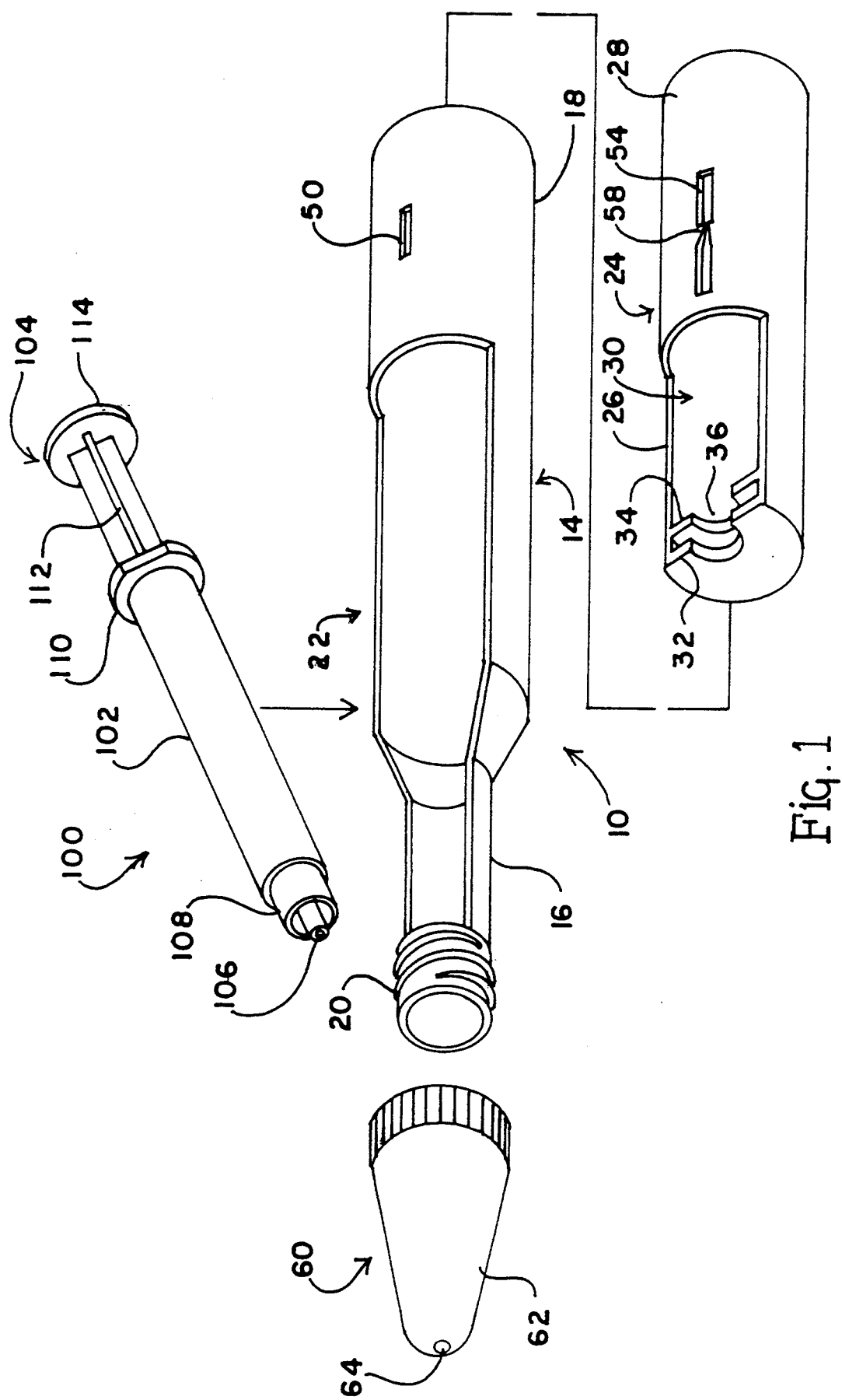
FIG. 1 is an exploded perspective view of a cartridge holder constructed according to the present invention.

In the following description, like reference characters designate like or corresponding parts throughout the several views. Also in the following description, it is to be understood that such terms as "forward", "rearward", "left" "right" "upwardly", "downwardly", and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIGS. 1-4, a preferred embodiment of the syringe holder 10 is shown. The syringe holder 10 is adapted to receive and hold a conventional disposable syringe 100 while administering medication to or drawing fluid from a patient.

The syringe 100 includes a generally cylindrical barrel 102 and a plunger 104 slidably mounted in the barrel 102. The forward end of the barrel 102 includes an aperture 106 through which the contents of the barrel 102 are dispensed. Surrounding the aperture 106 is the first half of a locking mechanism 108, such as a leur lock, for securing a hypodermic needle (not shown) to the barrel 102. The other half of the locking mechanism is attached to the proximal end of the needle.

The end of the barrel 102 opposite the needle is open to receive the plunger 104. A finger flange 110 projects radially outwardly from the barrel 102. The finger flange 110 is engaged by the index finger and middle finger during administration of medication or drawing fluid.

The plunger 104 includes an elongated shaft 112 having a thumb pad 114 at one end and a rubber piston (not shown) at the opposite end. The piston is slidable in the barrel 102 but seals against the inner surface of the barrel 102 so that when the plunger 104 is moved forwardly, the contents of the barrel 102 are displaced through the aperture 106.

In normal use, a hypodermic needle is attached to the forward end of the barrel 102. The needle will generally include a protective cover (not shown) which must be removed prior to administering medication to or drawing fluid from a patient. After the medication is administered or the fluid is drawn, the protective cover is reinserted over the needle and the syringe 100 is discarded. Many accidental needle pricks occur when attempting to reinsert the cover over the hypodermic needle. Further, medical personnel sometimes postpone covering the needle while attending to the needs of the patient leaving the needle exposed.

The syringe holder 10 of the present invention utilizes a needle assembly with a retractable needle to prevent accidental needle pricks. The needle assembly 60 mounts on a carrier 12 for receiving the hypodermic syringe 100. As will be hereinafter described, the hypodermic needle is exposed only when the hypodermic syringe is loaded into the carrier 12 and pushed forwardly and automatically retracts when the hypodermic syringe 100 is unloaded. Thus, the needle is exposed only while medication is being administered to or fluid is being drawn from the patient.

Referring now to the carrier 12, it includes an outer protective sleeve 14 and a plunger 24 slidably mounted in the protective sleeve 14. The protective sleeve 14 includes a forward portion 16 and a rear portion 18. The inside diameter of the forward portion 16 is sized to receive the barrel 102 of the syringe 100. External threads 20 are formed on the front end of the forward portion 16 for mounting the needle assembly 60. The rear portion 18 has a slightly larger diameter than the forward portion 16 and is sized to accommodate the finger flange 110 at the proximal end of the syringe barrel 102. A portion of the sleeve 14 is cut away to form a side opening 22. The side opening 22 permits loading and unloading of the hypodermic syringe 100 in a direction normal to the axis of the carrier 12. The side opening 22 extends from the ring 20 portion 16 into the rear portion 18. The side opening 22 should extend far enough into the rear portion 18 to accommodate a conventional hypodermic syringe 100 with the syringe plunger 104 fully extended.

A plunger 24 is slidably mounted in the rear portion 18 of the protective sleeve 14. The plunger 24 is generally cylindrical in configuration and is sized to slide freely within the rear portion 18 of the protective sleeve 14 between a "loading/unloading" position shown in FIG. 2, and a "use" position shown in FIG. 3. The plunger 24 has a front end 26 and a back end 28. The front end 24 is cut away to form a second side opening 30. The side opening 30 permits side loading of the hypodermic syringe in a direction normal to the axis of the carrier 12. A pair of semi-circular retaining walls 32 and 34 are disposed at the front end 26 of the plunger 24. Each retaining wall 32 and 34 includes a notch 36 to accommodate the barrel 102 and plunger 104 of syringe 100. The finger flange 110 of the syringe 100 is received between the retaining walls 32 and 34. The back end 28 of the plunger 24 is closed by an end wall 38.

The plunger 24 slides in the protective sleeve 14 between a "loading" position shown in FIG. 2, and a "use" position shown in FIG. 3. A locking mechanism 40 locks the plunger 24 in the "use" position. The locking mechanism 40 includes a resilient locking member 42 mounted in the rear portion 18 of the protective sleeve 14. The locking member 42 has a generally c-shaped configuration including a lower arm 44 and an upper arm 46. The lower arm 44 is secured to the inner surface of the protective sleeve 14 by an adhesive or other suitable means. A button 48 extends from the top side of the upper arm 46 through an opening 50 in the protective sleeve 14. A pair of ramps 52 extend outwardly from the end of the upper arm 46.

The plunger 24 includes a pair of longitudinally extending slots 54 and 56. Engagement of the locking member 42 with the ends of the slots 54 and 56 limits the forward and rearward movement of the plunger 24 in relation to the protective sleeve 14. A pair of tabs 58 extend into the slot 54 in the upper side of the plunger 24. When the plunger 24 is pushed forwardly, the tabs 58 engage the ramps 52 on the locking member 42. The tabs 58 ride over the ramps 52 causing the upper arm 46 of locking member 42 to flex downwardly. The upper arm 46 of the locking member 42 returns to its normal state after the tab 58 passes over the ramp 52 thereby locking the plunger 24 in the "use" position shown in FIG. 3. To move the plunger 34 back to the "loading/unloading" position, the button 48 on locking member 42 is manually pressed to flex the upper arm 46 downwardly, thereby allowing the tabs 58 to pass over the ramp 52 of the locking member 42.

The needle assembly 60 is mounted on the forward end of the carrier 14. The needle assembly 60 includes a needle cap 62. The needle cap 62 is conical in shape and has an aperture 64 at the forward end thereof. The rear end of the needle cap 62 includes threads 66 which engage with the threads 20 of the carrier 14. A coil spring 68 is mounted within the needle cap 62. One end of the coil spring 68 fits into a bore 70 in the needle cap 62. The opposite end of the coil spring 68 is attached to a standard hypodermic needle 72.

The hypodermic needle 72 includes a needle shaft 74 and a base 76. The base 76 includes one-half of a locking mechanism, such as a leur lock, that engages with the locking mechanism 108 on syringe 100. The hypodermic needle 72 extends axially through the opening in the coil spring 68 and aligns with the aperture 64 in the needle cap 60. The base 74 of the hypodermic needle 72 is held within the coil spring 58. The length of the coil spring 68 is at least as long as the needle 72 so that the needle 72 is normally retracted in the needle cap 62 and the coil spring 68 forms a sheath around the needle 72.

To use the syringe holder 10 of the present invention, the hypodermic syringe 100 is loaded into the carrier 12 through the side opening 22. When loading the hypodermic syringe 100, the finger flange 112 of the syringe 100 is inserted between the retaining walls 32, 34 of the plunger 24. After placing the hypodermic syringe 100 in the carrier 14, the needle assembly 60 is mounted to the carrier 14 by screwing the needle cap 62 onto the forward end 16 of the carrier sleeve 14. As the needle cap 62 is screwed onto the carrier sleeve 14, the base 64 of the needle 72 is simultaneously engaged with the leur lock 108 of the hypodermic syringe 100. Once the needle assembly 60 is securely in place, the plunger 24 is depressed pushing the hypodermic syringe 100 forwardly in the carrier sleeve 14. As the hypodermic syringe 100 is pushed forwardly, the coil spring 68 is compressed and the needle 72 is extended through the aperture 64 in the needle cap 62. The plunger 24 is pushed forwardly until the locking mechanism 40 engage locking the plunger 24 in a "use" position. The syringe 100 is then used in a normal manner to administer medication to or draw fluid from a patient. The side opening 22 in the carrier sleeve 14 allows manipulation of the syringe plunger 104.

After administration of the medication or drawing of the fluid, the release button 48 is depressed. When the release button 48 is depressed, the coil spring 68 pushes the hypodermic syringe 100 back to a loading/unloading position. As the hypodermic syringe 100 is moved back to the loading/unloading position, the needle 72 retracts into the needle cap 62. Thus, the used needle will be completely concealed by the needle cap 62 so that there is no chance of any medical professional accidently wounding himself with the used needle 72.

After use, the needle cap 62 is unscrewed from the carrier sleeve 14 and discarded along with the hypodermic syringe 100. The carrier 12 can be sterilized in an autoclave and reused many times.

Figure 5:
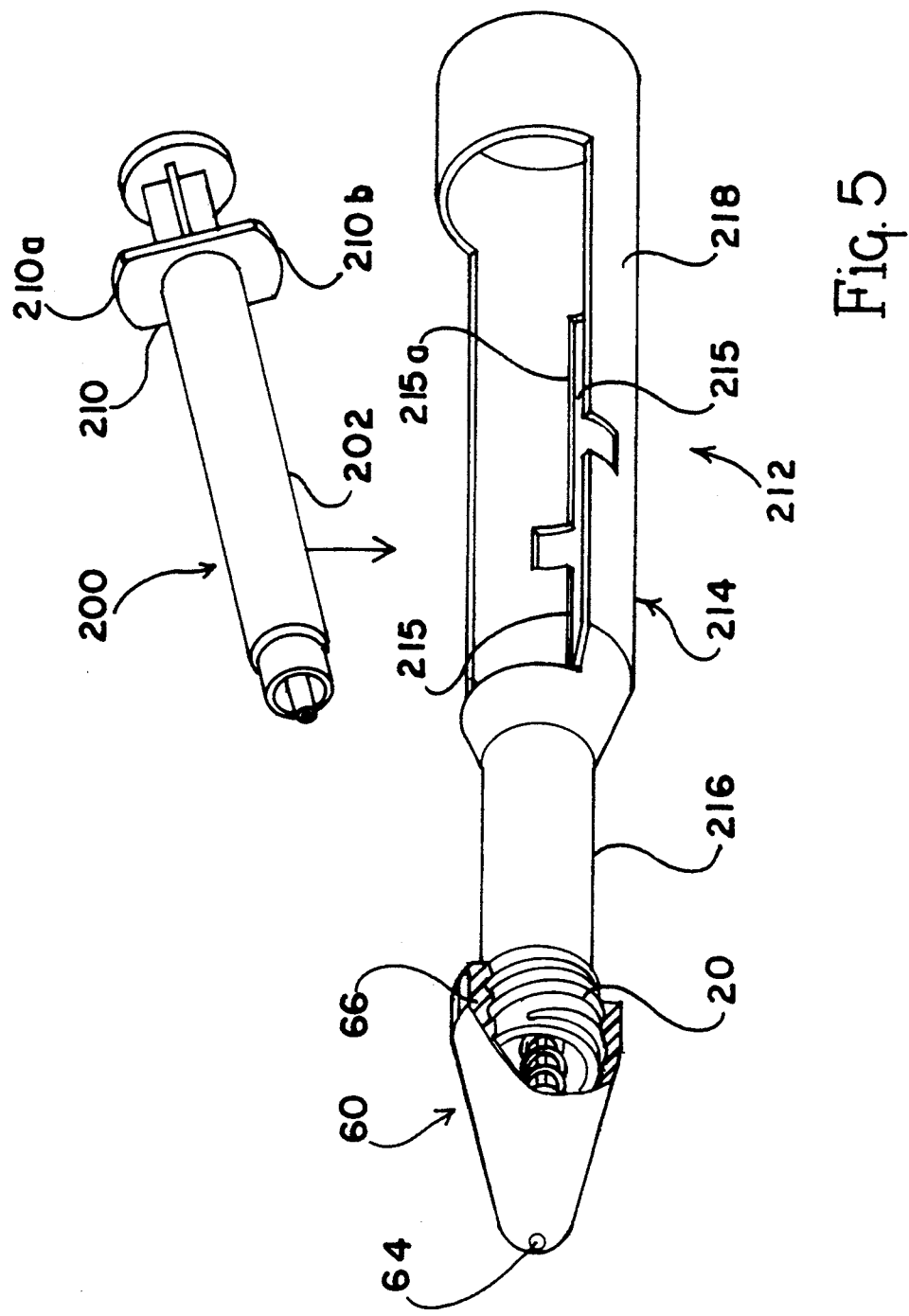
FIG. 5 is a perspective view illustrating a second embodiment of the syringe holder.

Referring to FIG. 5, a second embodiment of syringe holder 10 is shown. Syringe holder 10 of the second embodiment includes a carrier 212 for receiving a hypodermic syringe 200, and a needle assembly 60 having a retractable needle mounted at the forward end of the carrier 212. The needle assembly 60 is identical to needle assembly of the first embodiment.

Carrier 212 is designed particularly for syringes of the type having an elongated flange 210 with two opposing ends 210a, 210b. As in the first embodiment, the hypodermic needle is exposed only when the hypodermic syringe 200 is loaded and pushed forward in carrier 212, and automatically retracts when hypodermic syringe 200 is unloaded.

Carrier 212 includes a cylindrical protective sleeve 214 having a forward portion 216 and a rear portion 218. The inside diameter of the forward portion 216 is sized to receive the syringe 200. The forward end of the forward portion is threaded to allow mounting of the needle assembly 60. The rear portion 218 has a slightly larger diameter than the forward portion 216 and is sized to accommodate the finger flange 210 at the proximal end of the syringe barrel 202. A portion of the rear portion 218 is cut away to define a side opening 222. The side opening 222 extends along the rear portion 218 and is of a length sufficient to permit the insertion of the hypodermic syringe 200 into the carrier 214.

Sleeve 214 also includes a guide slot 215 that extends axially along outer protective sleeve 214. The guide slot 215 is disposed opposite the side opening 222. A pair of locking slots 217, 219 extend circumferentially from guide slot 215 and side opening 222, respectively. The locking slots 217, 219 divide the guide slot 215 into a forward section 215b and a rear section 215a. The width of the guide slot 215 is sized to receive the finger flange 210. Thus, guide slot 215 provides a guide for moving syringe 200 between a "loading/unloading" position and a "use" position.

In use, the syringe 200 is loaded into the carrier 212 by inserting it through the side opening 222 of the carrier 212. To insert the syringe 200 into the carrier, the finger flange 210 is rotated to align vertically with the guide slot 215. When the syringe 200 is initially loaded, the finger flange 210 lies somewhere in the rear section 215a of the guide slot. The needle assembly 60 is then attached to the forward end of the carrier 212. During mounting of the needle assembly 60, the hypodermic needle 72 is simultaneously engaged with the syringe 200.

To place syringe 200 in the "use" position, the syringe is pushed forwardly within the carrier 212 by manually pressing the finger flange 210 until the finger flange 210 reaches the locking slots 217, 219. The guide slot 215 guides the motion of the syringe 200. The syringe 200 is manually rotated upon reaching locking slots 217, 219 to lock opposing ends 210a, 210b of finger flange 210 within respective locking slots 217, 219 so as to prevent axial movement of syringe 200 within carrier 212.

The syringe 200 is then used in a normal manner to administer medication to or to draw fluid from a patient. After administration of the medication, the syringe 200 is rotated to disengage the finger flange 210 from the locking slots 217, 219. The coil spring 58 of the needle assembly pushes the hypodermic syringe 200 back to a "loading/unloading" position. As the hypodermic syringe 200 is moved back, the needle 72 retracts into the needle cap. The hypodermic syringe and needle cap are then removed and discarded. The carrier 212 can be sterilized in an autoclave and reused.

Based on the foregoing, it is apparent that the syringe holder of the present invention achieves the purpose of preventing accidental needle pricks by automatically retracting the hypodermic needle when the syringe is removed from the holder. Further, the syringe holder of the present invention can be used with conventional hypodermic syringes which are in wide-spread use in hospitals and doctors' offices. No modification of the conventional syringe is required.

Certain modifications and improvements will occur to those skilled in the art upon a reading of the foregoing description. By way of example, various materials could be used for the syringe holder including autoclavable plastics and stainless steel. It should be understood that all such modifications and improvements have been deleted herein for the sake of conciseness and readability but are properly within the scope of the following claims.

We claim:

1. A syringe holder comprising:
   (a) a carrier having a chamber sized for receiving and housing a hypodermic syringe including barrel and an extended syringe plunger, said syringe being moveable within said carrier between a loading-/unloading position and a use position;
   (b) a needle assembly detachably secured at a forward end of the carrier including a retractable needle normally disposed in a retracted position, said needle being moveable to an extended position when the syringe is moved from its loading/unloading position to its use position; and
   (c) a lock for locking the hypodermic syringe in its use position during administration of medication to a patient.

2. The syringe holder according to claim 1 wherein the carrier comprises a generally cylindrical sleeve with the interior of the sleeve defining a chamber for receiving the hypodermic syringe.

3. The syringe holder according to claim 2 further including a side opening formed in the sleeve to permit insertion and removal of the syringe into and from the chamber in a direction perpendicular to the axis of the sleeve.

4. The syringe holder according to claim 3 further including a plunger slidably mounted in said sleeve for moving the syringe between its loading/unloading position and its use position.

5. The syringe holder according to claim 4 wherein the lock means is operable to lock the plunger in a use position.

6. The syringe holder according to claim 3 wherein said sleeve includes a longitudinally extending guide slot for receiving a flange on said hypodermic syringe such that said flange projects outwardly through said guide slot.

7. The syringe holder according to claim 6 wherein the lock means comprises a locking slot for engaging the flange of a hypodermic syringe to lock the hypodermic syringe in a use position, said locking slot extending circumferentially from said guide slot.

8. A syringe holder comprising:
   (a) a carrier having an axis, a forward end, a rear end, and a chamber having a side opening for receiving a hypodermic syringe to permit insertion and removal of the syringe into and from the chamber transversely of the axis, said syringe being moveable within said chamber between a loading/unloading position and a use position;
   (b) a needle assembly detachably secured at said forward end of the carrier, said needle assembly including:
      (1) a needle cap having one closed end and one open end;
      (2) an aperture formed in the closed end of the needle cap;
      (3) a needle mounted within the needle cap so as to moveable between a retracted position within the needle cap and an extended position in which the needle projects through the aperture of the needle cap;
      (4) a coil spring for biasing the needle to its retracted position, said coil spring forming a longitudinally compressible sheath around the needle when the needle is in the retracted position; and
   (c) a lock for locking the hypodermic syringe in its use position during administration of medication to a patient.

9. The syringe holder according to claim 8 wherein the carrier comprises a generally cylindrical sleeve with the interior of the sleeve defining a chamber for receiving the hypodermic syringe.

10. The syringe holder according to claim 8 further including a plunger slidably mounted in said sleeve for moving the syringe between its loading/unloading position and its use position.

11. The syringe holder according to claim 8 wherein the lock means is operable to lock the plunger in a use position.

12. The syringe holder according to claim 8 wherein said sleeve includes a longitudinally extending guide slot for receiving a flange on said hypodermic syringe such that said flange projects outwardly through said guide slot.

13. The syringe holder according to claim 12 wherein the lock means comprises a locking slot for engaging the flange of a hypodermic syringe to lock the hypodermic syringe in a use position, said locking slot extending circumferentially from said guide slot.

14. A syringe holder comprising:
   (a) a carrier in the form of a sleeve having an axis with the interior of the sleeve defining a chamber for receiving a hypodermic syringe, the sleeve having a side opening for receiving a hypodermic syringe to permit insertion and removal of the syringe into and from the chamber transversely of the axis, said syringe being moveable within said carrier between a loading/unloading position and a use position;
   (b) a needle assembly detachably secured at a forward end of the carrier including a retractable needle normally disposed in a retracted position, said needle being moveable to an extended position when the syringe is moved from its loading/unloading position to its use position; and
   (c) a lock for locking the hypodermic syringe in its use position during administration of medication to a patient.

15. A syringe holder comprising:
   (a) a carrier having a chamber for receiving a hypodermic syringe, said syringe being moveable within said carrier between a loading/unloading position and a use position;
   (b) a plunger slidably mounted in said carrier for moving the syringe between its loading/unloading position and its use position,
   (c) a needle assembly detachably secured at a forward end of the carrier including a retractable needle normally disposed in a retracted position, said needle being moveable to an extended position when the syringe is moved from its loading/unloading position to its use position; and
   (c) a lock for locking the hypodermic syringe in its use position during administration of medication to a patient.

* * * * *